United States Patent
Mannaerts et al.

(10) Patent No.: US 6,653,286 B1
(45) Date of Patent: Nov. 25, 2003

(54) GONADOTROPIN RELEASING HORMONE ANTAGONIST

(75) Inventors: Bernadette Maria Julia Louise Mannaerts, Acacialaan; Herman Jan Tijmen Coelingh Bennink, Melvill van Carnebeelaan; Everardus Otto Maria Orlemans, Wolvespoor, all of (NL)

(73) Assignee: Akzo Nobel NV, Arnhem (NL)

( * ) Notice: Subject to any disclaimer, the term of this patent is extended or adjusted under 35 U.S.C. 154(b) by 0 days.

(21) Appl. No.: 09/446,324
(22) PCT Filed: Jun. 16, 1998
(86) PCT No.: PCT/EP98/03713
§ 371 (c)(1), (2), (4) Date: Dec. 20, 1999
(87) PCT Pub. No.: WO98/58657
PCT Pub. Date: Dec. 30, 1998

(30) Foreign Application Priority Data

Jun. 20, 1997 (EP) .............................. 97201885

(51) Int. Cl.$^7$ .......................... A61K 38/08; A61K 38/24
(52) U.S. Cl. .............................................. 514/15; 514/8
(58) Field of Search ....................... 514/15, 8

(56) References Cited

U.S. PATENT DOCUMENTS 4,801,577 A  1/1989  Nestor

OTHER PUBLICATIONS

Nelson et al., *Fertility and Sterility*, 63(5) :963–969 (1995).
Fujimoto et al., *Fertility and Sterility*, 67(3):469–473 (1997).

Primary Examiner—Christopher S. F. Low
Assistant Examiner—Billy Dell Chism
(74) Attorney, Agent, or Firm—William M. Blackstone

(57) ABSTRACT

The present invention relates to a method to prevent a premature LH surge. The method employs the administration of the gonadotropin releasing hormone antagonist ganirelix in an amount between 0.125–1 mg in combination with exogenous FSH. The method can be used in the treatment of women undergoing controlled ovarian superovulation.

4 Claims, 2 Drawing Sheets

GONADOTROPIN RELEASING HORMONE ANTAGONIST

FIELD OF THE INVENTION

The present invention relates to a pharmaceutical preparation useful in controlled ovarian hyperstimulation (COH) as well as to a method to prevent a premature LH surge.

BACKGROUND OF THE INVENTION

The glycoprotein hormones Luteinizing Hormone (LH) and Follicle Stimulating Hormone (FSH) are released from the pituitary gland under control of Gonadotropin Releasing Hormone (GnRH). They act on the ovary to stimulate steroid synthesis and secretion and thus play a central role in the reproductive cycle.

In the normal cycle, there is a mid-cycle surge in LH concentration which is followed by ovulation. The LH surge is a consequence of the raise in estrogen levels brought about by the endogenous secretion of LH and FSH. The estrogen is part of a positive feedback mechanism resulting in the elevated LH level.

GnRH analogues are useful for a variety of disorders in which immediate reversible suppression of the pituitary-gonadal axis is desired. This can in principle be achieved with GnRH agonists as well as with GnRH antagonists. In comparison to GnRH agonists, GnRH antagonists have the advantage of not inducing an initial release of gonadotropins (flare-up) and steroids before suppression.

Currently, GnRH agonists are clinically applied for the prevention of endogenous LH-surges during controlled ovarian hyperstimulation for Assisted Reproduction Techniques (ART). Specific disadvantages of GnRH agonists are the initial flare-up and the rather long period until pituitary suppression becomes effective. Usually, patients undergoing COH start only treatment with (recombinant) FSH after 2 to 3 weeks pretreatment with GnRH agonists.

Women treated for this purpose without GnRH analogues, all show attenuated LH rises irrespective of the treatment schedule used. Usually these rises occur prematurely due to a positive feedback of rising estradiol (E2) produced by a cohort of relative small follicles. The exposure of non-mature follicles to high levels of LH leads to premature luteinisation of granulosa cells and hence to increased production of progesterone and decreased synthesis of E2. These changes lead to disrupted maturation and decreased fertilization and implantation rates. Success rates of COH cycles in which premature LH rises are detected, are reported to be low and often these cycles are canceled because the number and/or size of follicles is still too small.

The suppressive potency of GnRH agonist treatment in women with normal menstrual cycles may depend on structure-receptor interaction, elimination half-life dosage and route of administration of the specific GnRH agonist applied. Clinical studies with different regimens of GnRH agonists have clearly demonstrated that the amount of remaining LH in women undergoing COH is always sufficient to support folliculogenesis and estrogen biosynthesis induced by pure FSH. In these studies the minimum amount of circulating endogenous LH was only 1 to 2 IU/L. In some women LH concentrations dropped below 0.5 IU/L but still FSH treatment appeared to be effective.

In contrast to GnRH agonists, GnRH antagonists by GnRH receptor competition provide an immediate inhibition of gonadotropin secretion, especially of LH. Thus, during COH by FSH, GnRH antagonist treatment is only required during the few days when there is an increased risk for a premature LH surge.

SUMMARY OF THE INVENTION

The present invention relates to the use of the antagonist ganirelix which has the following chemical name:

N-Acetyl-3-(2-naphtyl)-D-alanyl-4-chloro-D-phenylalanyl-3-(3-pyridyl)-D-alanyl-L-seryl-L-tyrosyl-$N^{\omega}$,$N^{\omega}$-diethyl-D-homoarginyl-L-leucin-$N^{\omega}$, $N^{\omega}$-diethyl-L-homoarginyl-L-propyl-D-alanylamide acetate. The abbreviated structure is (N-Ac-D-Nal(2)$^1$, D-pClPhe$^2$D-Pal(3)$^3$,D-hArg(Et$_2$)$^6$,L-hArg(Et$_2$)$^8$,D-Ala$^{10}$)-GnRH.

In a phase I study, published by Nelson et al., 1995, rapid, profound, reversible suppression of the pituitary-gonadal axis was obtained in reproductive age women. In this study women started on days 6 to 9 of the menstrual cycle with a daily SC injection of 1 mg or 2 mg of GnRH ganirelix for 8 consecutive days. Nelson et al demonstrated that maximal mean LH suppression was approximately 60% at 8 h after the first injection and that at that time point LH levels were 4 to 5 IU/L. During the treatment period, serum LH measured just prior to the following administration of ganirelix remained at steady state (5 to 6 IU/L) at a dose of 2 mg ganirelix whereas those treated with 1 mg ganirelix showed slowly increasing concentrations of endogenous LH (from 6 to 9 IU/L)

The GnRH antagonist ganirelix is disclosed in U.S. Pat. No. 4,801,577 for nonapeptide and decapeptide analogs of LHRH useful as LHRH antagonists. This patent, which is fully incorporated herein by reference, describes the method for the preparation of these compounds. It is indicated that the compounds described therein can be used for the prevention of ovarian hyperstimulation. For human therapy a daily range is suggested for administration of the active ingredient between 0.001 and 5 mg/kg body weight, preferably between 0.01 and 1 mg/kg.

Surprisingly, however, clinical experiments have indicated that the dosage range is very narrow and that a deviation from this range is either leading to premature LH rises or to too much suppression of endogenous LH and as a consequence of estrogen biosynthesis. Accordingly, the implantation rate is unacceptable low. In contrast, a daily dose between 0.125 mg and 1 mg of ganirelix per subject on one hand prevents premature LH rises to occur and at the same time maintains sufficient LH to support follicular maturation and estrogen biosynthesis, both required to ensure successful treatment outcome.

DETAILED DESCRIPTION OF THE INVENTION

Figure 1:
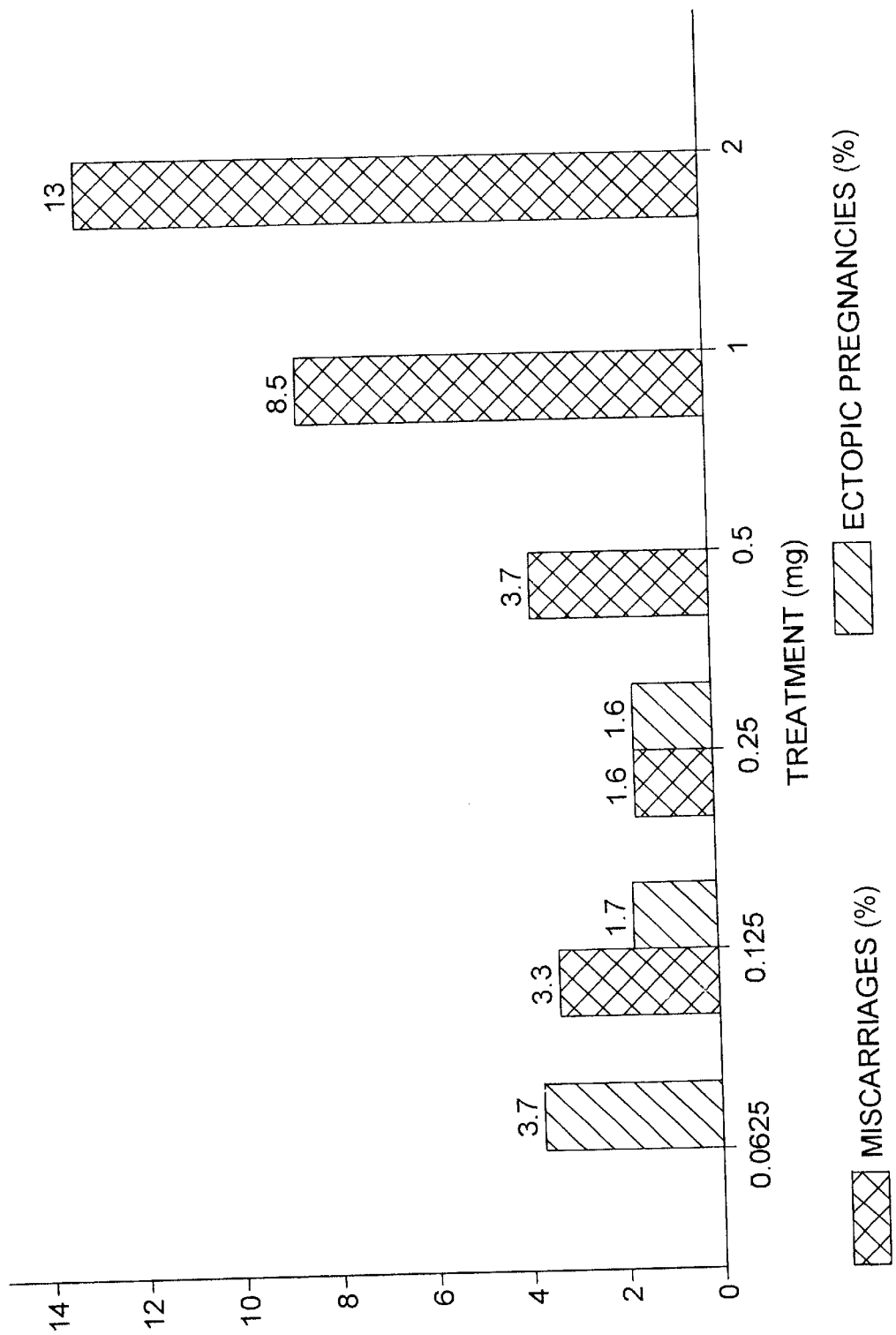
FIG. 1: Miscarriage rate and Ectopic pregnancy rate per treatment for each dosage group of ganirelix.

The invention therefore relates to a pharmaceutical preparation comprising ganirelix in an amount which is at least 0.125 mg but less than 1 mg. Preferably the amount is about 0.25 mg. This preparation is useful in the treatment of women undergoing COH.

The preparation is administered together with FSH during the days of ovarian stimulation when a premature LH rise may easily occur e.g. from day 5 of FSH administration onwards. The preparation in its proposed dosage range has the advantage of providing an immediate effect that prevents an LH surge and at the same time maximizes the chances of establishing pregnancy. Administration is usually stopped when sufficient follicles have matured and exogenous hCG/LH is given for induction of ovulation.

The exact regimen for administration might depend on the individual response and is finally to be decided by the clinician who treats the subject. For this reason the duration of initial ovarian stimulation with FSH alone as well as the duration of combined treatment with FSH/GnRH antagonist treatment may vary. FSH treatment usually starts at menses day 1, 2 or 3. Ovarian stimulation with FSH alone may be continued up to 5 days in an amount of 150–225 IU. FSH is administered preferably as a recombinant protein. Treatment with GnRH antagonist may be started at the first day of FSH, but preferably such treatment starts at FSH treatment day 4 or 5. The GnRH antagonist is administered in the amount as indicated in combination with FSH in amounts between 75–600 IU, preferably between 150–300 IU. GnRH antagonist treatment may last 2–14 days i.e. up to the moment whereupon the patient is treated with exogenous LH/hCG for ovulation induction.

According to another aspect of the invention ganirelix in an amount of 0.125–1 mg is used for the manufacture of a medicament to prevent a premature LH surge in women undergoing controlled ovarian hyperstimulation.

The pharmaceutical preparations for use according to the invention can be prepared in accordance with standard techniques such as for example are described in the standard reference, Gennaro et al. (Ed.), Remmington's Pharmaceutical Sciences, (18$^{th}$ ed. Mack Publishing Company, 1990, e.g. Part 8: Pharmaceutical Preparations And Their Manufacture). For the purpose of making the pharmaceutical preparations according to the invention, the active substance is mixed with or dissolved in a pharmaceutical acceptable carrier.

Any conventional pharmaceutical carrier that does not interfere with performance of the active ingredient can be used in the preparations according to the present invention. Formulations may contain as common excipients sterile water or saline, alkylene glycols such as propylene glycol, polyalkylene glycols such as polyethylene glycol, oils of vegetable origin, hydrogenated naphtalenes and the like.

The pharmaceutical preparation may be administered parenterally. Preferably it is administered subcutaneously, particularly in the form of liquid solutions or suspensions. A typical formulation is a solution containing, in addition to the active substance in an amount of 0.125–1 mg, glacial acetic acid, mannitol, and water adjusted to pH 5 with sodium hydroxide and/or hydrochloric acid. Optionally preservations such as e.g. methyl- and propylparaben can be added. The solutions can be packaged e.g. in glass vials or in syringes.

Legends to the Figures

FIG. 1: Miscarriage rate and Ectopic pregnancy rate per treatment for each dosage group of ganirelix.

Figure 2:
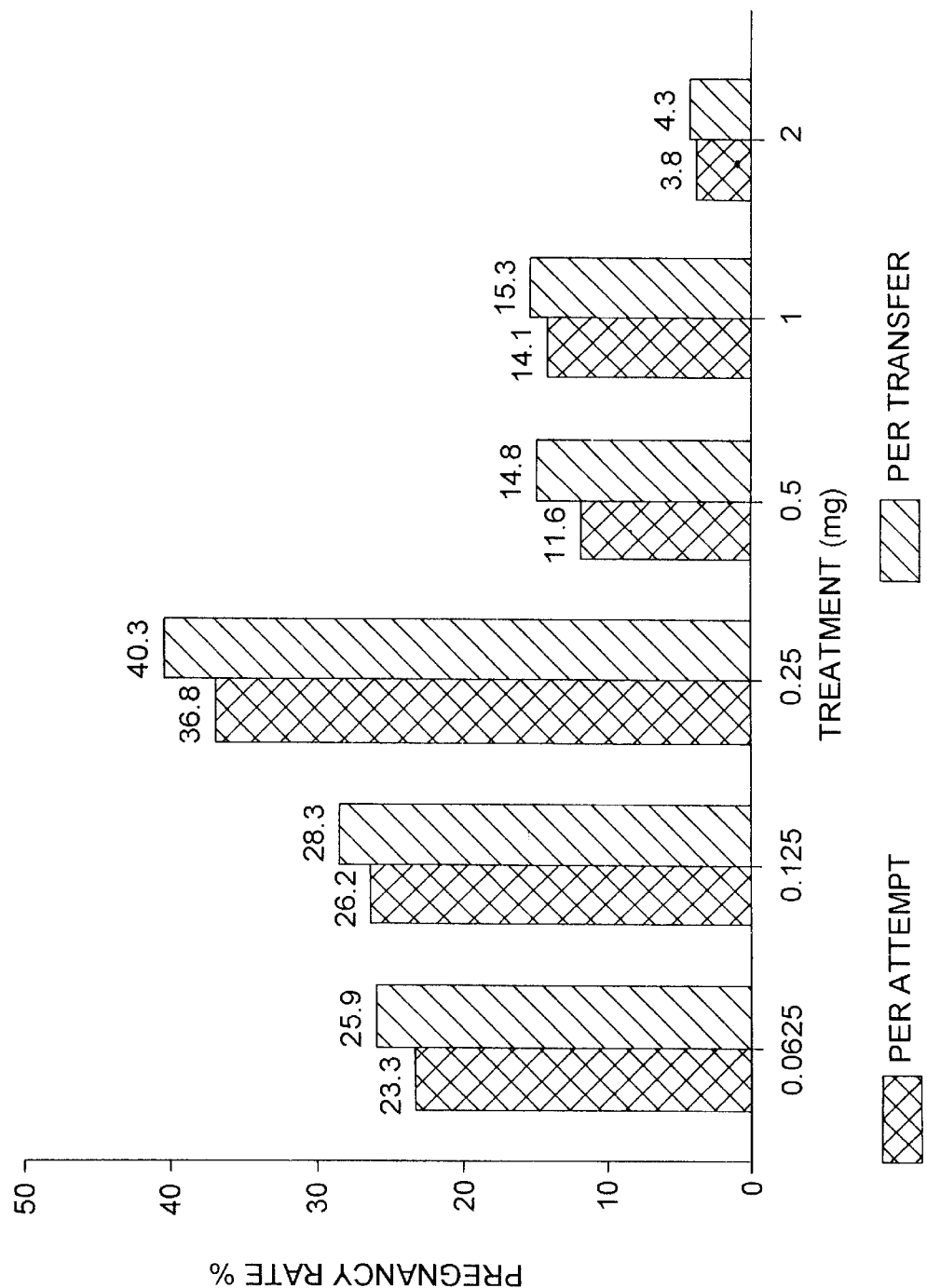
FIG. 2: Vital Pregnancy rate per attempt (those who started hormonal treatment) and per transfer (those who indeed had embryo transfer) for each dosage group of ganirelix.

FIG. 2: Vital Pregnancy rate per attempt (those who starting hormonal treatment) and per transfer (those who indeed had a embryo transfer) for each dosage group of ganirelix.

EXAMPLES

In order to establish the minimum effective dose of ganirelix to prevent premature LH surges in women undergoing COH with recombinant FSH, a double-blind dose-finding study was performed with 6 test doses ranging between 2 mg and 0.0625 mg ganirelix.

This study was a phase II, multi-centre, double-blind, randomized, dose-finding study to assess the efficacy of the GnRH-antagonist ganirelix to prevent premature LH surges in women undergoing controlled ovarian hyperstimulation with recFSH. The dosages of ganirelix are administered by one daily SC administration.

RecFSH treatment started on day 2 of the menstrual cycle (treatment day -5) by a once daily SC injection. From treatment day -5 through day -1 the dose of recFSH was fixed at 150 IU daily. After 5 days of recFSH treatment (day 7 of the menstrual cycle), ganirelix treatment was started by daily SC administration. Treatment continued until and including the last day of recFSH administration. During ganirelix treatment, the dose of recFSH was adjusted depending on the individual ovarian response as assessed by daily ultra sonographic scan (USS). As soon as at least 3 folicles ≧17 mm measured by USS were observed, hCG was administered for ovulation induction. About 30–36 hours thereafter oocyte pick-up was performed followed by in vitro fertilization (IVF) with or without intracytoplasmic sperm injection (ICSI). No more than 3 embryos were replaced.

If during ganirelix treatment a premature LH rise occurred e.g. at least one value of serum LH ≧15 IU/L according to the local LH immunoassay the investigator canceled the cycle or tried to rescue the cycle by giving hCG prematurely. In addition, the investigator notified the sponsor about the occurrence of the LH rise and the central laboratory was requested to confirm the LH rise was ≧10 IU/L according to the central LH immunoassay. Subsequently, all data of such subject with a premature LH rise were forwarded to an Independent Advisory Committee which was installed in order to advice on stopping a treatment arm in case of LH rises during ganirelix treatment.

During the study, some investigators informed the sponsor on one or more cases of extremely low serum LH and failing estradiol concentrations as well as follicle growth arrest after starting ganirelix treatment. For this reason the External Independent Advisory Committee was requested to review all clinical data available in order to evaluate whether these observations were dose related and whether, in their opinion, there was reason to stop one or more treatment arms.

In addition, the Independent Advisory Committee reviewed all rises of LH (≧15 IU/L according to the local LH immunoassay and ≧10 IU/L according to the central LH immunoassay) during ganirelix treatment. Based on their evaluation the External Committee advised the sponsor to stop the highest (2 mg) and lowest (0.0625 mg) treatment dose of ganirelix. The study was completed for the other dosage groups.

In total 333 subjects started recFSH treatment and 332 subjects started ganirelix treatment. Because of major protocol violation 3 subjects were excluded from the analysis. The final number of patients per dosing group are included in Table 1.

Serum ganirelix concentration increased in a dose-proportional manner and showed a negative relationship with serum LH concentrations. The lowest dose of 0.0625 mg ganirelix could not prevent LH rises to occur in 5 out of 31 subjects (16%) (see Table 1).

During ovarian stimulation with FSH increases of serum estradiol were lower with increasing doses of ganirelix. Accordingly, at the day of hCG, median LH and estradiol values were most decreased in the 2 mg group resulting in very low values of 0.34 IU/L and 430 pg/ml, respectively (see Table 2). In this group 4 women were switched during ovarian stimulation from FSH to hMG (human menopausal gonadotropin) to increase LH concentrations and to ensure sufficient estrogen production. Although a similar number of good quality embryos was obtained and used for transfer, in the 2 mg dose group the miscarriage rate was highest (13%) and the vital pregnancy rate was lowest i.e. 3.8% per attempt and 4.3% per transfer (see FIGS. 1 and 2).

TABLE 1

Incidence of LH rises in the different ganirelix dosage groups.

| Dose group | 0.0625 mg N = 31 | 0.125 mg N = 65 | 0.25 mg N = 69 | 0.5 mg N = 69 | 1 mg N = 65 | 2 mg N = 30 |
|---|---|---|---|---|---|---|
| | 5 (16%) | 6 (9.2%) | 1 (1.4%) | 0 | 0 | 0 |

TABLE 2

Median serum hormone values at the day of hCG (= last day of ganirelix)

| Hormone value | 0.0625 mg | 0.125 mg | 0.25 mg | 0.5 mg | 1 mg | 2 mg |
|---|---|---|---|---|---|---|
| FSH IU/L | 9.1 | 9.0 | 9.1 | 10.2 | 9.8 | 8.8 |
| LH IU/L | 3.56 | 2.46 | 1.73 | 1.02 | 0.57 | 0.34 |
| $E_2$ pg/ml | 1475 | 1130 | 1160 | 823 | 703 | 430 |

What is claimed is:

1. A method for attenuating LH rise in women undergoing controlled ovarian hyperstimulation by administering exogenous FSH, said method comprising administering cojointly FSH and parenterally administering ganirelix in a daily dose of between 0.125 mg and 0.5 mg.

2. The method of claim 1, wherein the daily dose is 0.25 mg.

3. The method of claim 1, wherein said parenteral administration is subcutaneous.

4. The method of claim 1, wherein said ganirelix is is administered cojointly with FSH for 2–14 days.

* * * * *